US009476819B2

(12) United States Patent
Wang et al.

(10) Patent No.: US 9,476,819 B2
(45) Date of Patent: Oct. 25, 2016

(54) HYDRODYNAMIC PARTICLE SEPARATION AND DETECTION SYSTEMS AND METHODS

(75) Inventors: Tza-Huei Jeff Wang, Timonium, MD (US); Kelvin Jeng-Fang Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 629 days.

(21) Appl. No.: 13/822,986

(22) PCT Filed: Oct. 19, 2011

(86) PCT No.: PCT/US2011/056941
§ 371 (c)(1),
(2), (4) Date: Mar. 13, 2013

(87) PCT Pub. No.: WO2012/054641
PCT Pub. Date: Apr. 26, 2012

(65) Prior Publication Data
US 2013/0167623 A1    Jul. 4, 2013

Related U.S. Application Data
(60) Provisional application No. 61/394,585, filed on Oct. 19, 2010.

(51) Int. Cl.
*G01N 15/14* (2006.01)
*C12Q 1/68* (2006.01)
(Continued)

(52) U.S. Cl.
CPC ........... *G01N 15/1484* (2013.01); *C12Q 1/686* (2013.01); *G01N 21/645* (2013.01);
(Continued)

(58) Field of Classification Search
CPC ...................... G01N 33/48; G01N 2015/1493; G01N 2015/1484; G01N 2015/149
See application file for complete search history.

(56) References Cited

U.S. PATENT DOCUMENTS

2002/0179849 A1   12/2002   Maher et al.
2010/0118300 A1    5/2010   Wang et al.

FOREIGN PATENT DOCUMENTS

WO    WO-2010/101926 A2    9/2010

OTHER PUBLICATIONS

Wang, Xiayan et al., "Free Solution Hydrodynamic Separation of DNA Fragments from 75 to 106,000 Base Pairs in a Single Run" including Supporting Information, JACS Communications, Dec. 16, 2009.*

(Continued)

*Primary Examiner* — Paul West
(74) *Attorney, Agent, or Firm* — Venable LLP; Henry J. Daley

(57) ABSTRACT

A method of separating, detecting and determining a size of each of a plurality of particles in a fluid includes compelling the fluid to flow through a fluid channel such that larger particles of the plurality of particles travel through the fluid channel faster than smaller particles of the plurality of particles; illuminating a detection zone of the fluid channel substantially uniformly across an entire cross section of the fluid channel such that each of the plurality of particles passes through illumination light upon passing through the detection zone; detecting each of the plurality of particles based on corresponding responses to the illuminating to determine a time that each of the plurality of particles passes through the detection zone; and determining a size of each of the plurality of particles based on the time that each of the plurality of particles passes through the detection zone.

19 Claims, 11 Drawing Sheets

(51) Int. Cl.
*G01N 21/64* (2006.01)
*G01N 33/48* (2006.01)
*G01N 15/02* (2006.01)

(52) U.S. Cl.
CPC ......... *G01N 33/48* (2013.01); *G01N 15/0255* (2013.01); *G01N 2015/149* (2013.01); *G01N 2015/1486* (2013.01); *G01N 2015/1493* (2013.01)

(56) References Cited

OTHER PUBLICATIONS

Liu, Kelvin J. et al., "Cylindrical Illumination Confocal Spectroscopy: Rectifying the Limitations of Confocal Single Molecule Spectroscopy through One-Dimensional Beam Shaping", Biophysical Journal, vol. 95, Sep. 2008.*
Chen et al., Analytical Chemistry 1996, 68, 690-696.
Effenhauser et al., Analytical Chemistry 1997, 69, 3451-3457.
Finney, M. Pulsed-Field Gel Electrophoresis; John Wiley & Sons, Inc., 2001.
Frost et al., Anal Chem May 2010, 82, 4682-98.
Glazer, A. N.; Rye, H. S. Nature 1992, 359, 859-61.
Haab, B. B.; Mathies, R. A. Anal Chem 1995, 67, 3253-60.
Haab, B. B.; Mathies, R. A. Anal Chem 1999, 71, 5137-45.
Iki, N.; Kim, Y.; Yeung, E. S. Analytical Chemistry 1996, 68, 4321-4325.
Kim, Y.; Morris, M. D. Anal Chem 1994, 66, 1168-74.
Kostal, V.; Katzenmeyer, J.; Arriaga, E. A. Anal Chem 2008, 80, 4533-50.
Liu, K. J.; Brock, M. V.; Shih le, M.; Wang, T. H. J Am Chem Soc 2010, 132, 57938.
Liu, K. J.; Wang, T. H. Biophys J 2008, 95, 2964-75.
Liu, K.J. et al., "Single-Molecule Analysis Enables Free Solution Hydrodynamic Separation Using Yoctomole Levels of DNA," J. Am. Chem. Soc, Apr. 2011, vol. 133, 6898-6901.
Santangelo, P. J.; Nix, B.; Tsourkas, A.; Bao, G. Nucleic Acids Res 2004, 32, e57.
Stein, D.; van der Heyden, F. H.; Koopmans, W. J.; Dekker, C. Proc Natl Acad Sci U S A 2006, 103, 15853-8.
Tijssen, R.; Bos, J.; van Kreveld, M. E. Anal Chem 1986, 58, 3036-3044.
Voytas, D. Agarose Gel Electrophoresis; John Wiley & Sons, Inc., 2001.
Wang et al., J Am Chem Soc 2005, 127, 15664-5.
Wang et al., "Free Solution Hydrodynamic Separation of DNA Fragments from 75 to 106 000 Base Pairs in a Single Run," J. Am. Chem. Soc., 2009, vol. 132, 40-41.
Wang et al., Anal Chem 2008, 80, 5583-9.
Xi et al., Appl Environ Microbiol 2003, 69, 5673-8.
Zhang et al., Nat Mater 2005, 4, 826-31.

* cited by examiner

HYDRODYNAMIC PARTICLE SEPARATION AND DETECTION SYSTEMS AND METHODS

CROSS-REFERENCE OF RELATED APPLICATION

This application claims priority to U.S. Provisional Application No. 61/394,585 filed Oct. 19, 2010, the entire contents of which are hereby incorporated by reference, and is a U.S. national stage application under 35 U.S.C. §371 of PCT/US2011/056941, filed Oct. 19, 2011, the entire contents of which are incorporated herein by reference.

This invention was made with Government support of Grant No. R21CA120742, awarded by the Department of Health and Human Services, The National Institutes of Health (NIH); and Grant No. 0546012, awarded by NSF. The U.S. Government has certain rights in this invention.

BACKGROUND

1. Field of Invention

The field of the currently claimed embodiments of this invention relates to systems and methods for separating and determining sizes of particles in a sample, and more particularly hydrodynamic systems and methods for separating and determining sizes of particles in a sample.

2. Discussion of Related Art

The dominant conventional methods of DNA sizing and separation are dependent on electrophoresis and/or chromatography. The most common method, slab gel electrophoresis, is convenient but has limited DNA sizing resolution, poor detection sensitivity, limited quantitative accuracy, and cannot be used to size large DNA molecules. Pulsed field gel electrophoresis can be used to size large DNA molecules but has long run times and poor quantitative accuracy. Capillary electrophoresis (CE) has very high DNA sizing resolution, high detection sensitivity, and fast run times. However, it is complex and requires expensive instrumentation, viscous sieving matrices, and functionalized capillaries. Reproducibility can also be problematic due to sensitivity to capillary wall properties.

Capillary electrophoresis remains the most widely used analytical method for high-resolution separation of DNA and other biological molecules. With the help of laser-induced fluorescence (LIF), the detection limit can be reduced to typical levels of $10^{-18}$ to $10^{-21}$ mol (Kostal, V.; Katzenmeyer, J.; Arriaga, E. A. Anal Chem 2008, 80, 4533-50; Frost, N. W.; Jing, M.; Bowser, M. T. Anal Chem 2010, 82, 4682-98) and single-molecule capillary electrophoresis SM-CE becomes possible (Haab, B. B.; Mathies, R. A. Anal Chem 1999, 71, 5137-45; Haab, B. B.; Mathies, R. A. Anal Chem 1995, 67, 3253-60; Effenhauser, C. S.; Bruin, G. J. M.; Paulus, A.; Ehrat, M. Analytical Chemistry 1997, 69, 3451-3457; Chen, D.; Dovichi, N. J. Analytical Chemistry 1996, 68, 690-696). Such techniques are limited by low mass detection efficiency (<1%), narrow DNA sizing dynamic range, the necessity for viscous sieving matrices, and the complexities of high voltage injection and separation schemes.

There thus remains a need for improved systems and methods for separating and determining sizes of particles in a sample.

SUMMARY

A method of separating, detecting and determining a size of each of a plurality of particles in a fluid according to an embodiment of the current invention includes compelling the fluid to flow through a fluid channel such that larger particles of the plurality of particles travel through the fluid channel faster than smaller particles of the plurality of particles; illuminating a detection zone of the fluid channel substantially uniformly across an entire cross section of the fluid channel such that each of the plurality of particles passes through illumination light upon passing through the detection zone; detecting each of the plurality of particles based on corresponding responses to the illuminating to determine a time that each of the plurality of particles passes through the detection zone; and determining a size of each of the plurality of particles based on the time that each of the plurality of particles passes through the detection zone.

A system for separating, detecting and determining a size of each of a plurality of particles in a fluid according to an embodiment of the current invention includes a hydrodynamic fluid separation system comprising a fluid channel; an illumination system arranged to illuminate a detection zone of the fluid channel substantially uniformly across an entire cross section of the fluid channel such that each of the plurality of particles passes through illumination light upon passing through the detection zone; a detection system arranged to detect each of the plurality of particles based on corresponding responses to the illumination light to determine a time that each of the plurality of particles passes through the detection zone; and a data processing system adapted to communicate with the detection system and configured to determine a size of each of the plurality of particles based on the time that each of the plurality of particles passes through the detection zone.

BRIEF DESCRIPTION OF THE DRAWINGS

Further objectives and advantages will become apparent from a consideration of the description, drawings, and examples.

(FIG. 9B) 1.26:1 bp:dye staining ratio (0.25 ng/μL DNA and 0.3 μM TOTO-3 dye). At low bp:dye staining ratios, increased amounts of background DNA are seen between the separated peaks.

DETAILED DESCRIPTION

Figure 1:
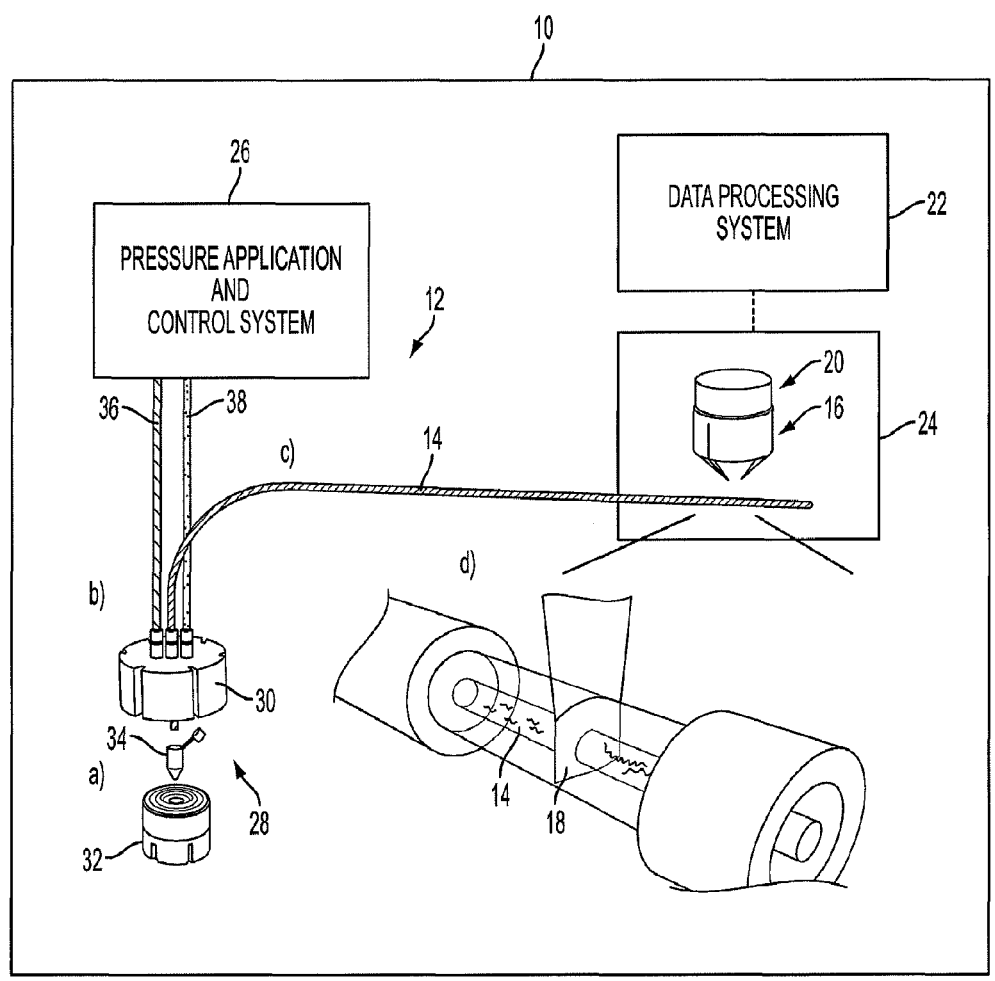
FIG. 1 is a schematic illustration of a system according to an embodiment of the current invention for separating, detecting and determining a size of each of a plurality of particles in a fluid.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The terms light, optical, optics, etc. are not intended to be limited to only visible light in the broader concepts. For example, they could include infrared and/or ultraviolet regions of the electromagnetic spectrum according to some embodiments of the current invention.

Some embodiments of the current invention are directed to hydrodynamic systems and methods for separating and determining sizes of particles in a sample. Some embodiments of the current invention can provide a method for single molecule analysis of size-separated DNA that surpasses the performance of Single Molecule Capillary Electrophoresis (SM-CE). By integrating cylindrical illumination confocal spectroscopy (CICS) (Liu, K. J.; Brock, M. V.; Shih Ie, M.; Wang, T. H. J Am Chem Soc 2010, 132, 5793-8; Liu, K. J.; Wang, T. H. Biophys J 2008, 95, 2964-75) with free solution hydrodynamic separation (Wang, X.; Veerappan, V.; Cheng, C.; Jiang, X.; Allen, R. D.; Dasgupta, P. K.; Liu, S. J Am Chem Soc 2010, 132, 40-1; Iki, N.; Kim, Y.; Yeung, E. S. Analytical Chemistry 1996, 68, 4321-4325) according to an embodiment of the current invention, we have demonstrated size-specific single molecule analysis of DNA that required <100 molecules per band and picoliters of sample in an exemplar embodiment of the current invention. CICS has a sheet-like observation volume that enables substantially 100% detection efficiency of single molecules within the separation capillary in contrast to standard laser-induced fluorescence (LIF). In addition, direct single molecule counting can improve quantitative accuracy by eliminating reference curves and decoupling fluorescent intensity from abundance according to some embodiments of the current invention. This method was used to separate both large (23 vs. 27 kbp) and small DNA (100 vs. 200 bp) under the same conditions and required only inexpensive microcapillary, simple pressure control, and standard buffers in some examples according to an embodiment of the current invention. This technique was also used in a single molecule assay to detect a bacterial 16srRNA sequence with molecular beacon nanosensors according to an embodiment of the current invention. Because the separation was non-denaturing, we were able to investigate the thermodynamic equilibrium between molecular beacons in the bound-open state versus unbound-stochastically open state.

Single molecule free solution hydrodynamic separation (SML-FSHS) according to some embodiments of the current invention combines cylindrical illumination confocal spectroscopy based single molecule analysis with free solution hydrodynamic separation. CICS based single molecule analysis can increase detection sensitivity 2-3 orders of magnitude over previous demonstrations of FSHS. SML-FSHS, according to some embodiments of the current invention, possesses the high sensitivity and sizing resolution of capillary electrophoresis, the wide dynamic range of pulsed-field gel electrophoresis, and the simplicity and low cost of slab gel electrophoresis. Thus, it can provide new DNA sizing and separation techniques that have the highest sensitivity (~100 molecules), highest sizing resolution, largest dynamic range (~30 kbp), and lowest sample consumption (5 picoliter) compared to conventional methods.

SML-FSHS incorporates single molecule based counting of the size separated particles (e.g., DNA) rather than bulk fluorescence/intensity based analysis. This can make quantification much more accurate because fluorescent intensity and quantity are decoupled to eliminate the need for tedious calibrations. In addition, it can also provide increased sensitivity.h FIG. 1 is a schematic illustration of a system 10 for detecting and determining a size of each of a plurality of particles in a fluid according to an embodiment of the current invention. The system 10 includes a hydrodynamic fluid separation system 12 that has a fluid channel 14, an illumination system 16 arranged to illuminate a detection zone 18 of the fluid channel 14 substantially uniformly across an entire cross section of the fluid channel 14 such that each of the plurality of particles passes through illumination light upon passing through the detection zone 18, and a detection system 20 arranged to detect each of the plurality of particles based on corresponding responses to the illumination light to determine a time that each of the plurality of particles passes through the detection zone 18. The system 10 also includes a data processing system 22 adapted to communicate with the detection system 20 and configured to determine a size of each of the plurality of particles based on the time that each of the plurality of particles passes through the detection zone 18. The illumination system 16 can be a cylindrical illumination system according to an embodiment of the current invention. The illumination system 16 and the detection system 20 can be part of a confocal spectroscopy system 24 according to an embodiment of the current invention. In some embodiments of the current invention, the confocal spectroscopy system 24 can be a CICS system.

In some embodiments of the current invention, the system 10 can further include a pressure application and control system 26 operatively connected to the hydrodynamic fluid separation system 12. In the example shown in FIG. 1, the hydrodynamic fluid separation system 12 also includes a pressure vessel 28 that has an upper portion 30 and a lower portion 32 that fasten together to contain a sample and sample holder 34 therein. The pressure vessel 28 is operatively connected to pressure application and control system 26 by pressurizing tube 36 and pressure monitoring tube 38. The pressurizing tube 36 and pressure monitoring tube 38 and fluid channel 14 can be fused silica tubes, for example. However, the hydrodynamic fluid separation system 12 is not limited to this particular embodiment.

The pressure application and control system 26 can include pumps, pressure sources, pressure regulators, valves, and gauges for manual control, or could be further configured to provide automated or semi-automated control. For example, stable and precise control over timing, magnitude and time-dependent ramp up and down of applied pressure can all be important factors in achieving good particle separation, accurate size determinations, accurate quantification, and reproducible results.

The fluid channel 14 can be filled with buffer, water, acid, base, alcohol, organic solvents, and/or aqueous solvents, etc. In addition, the properties of the walls of the fluid channel 14 can be modified (e.g., covalently, coatings, passivation, electrostatically, charged, etc) to aid separation.

Figures 2A, 2B, 2C, 2D:
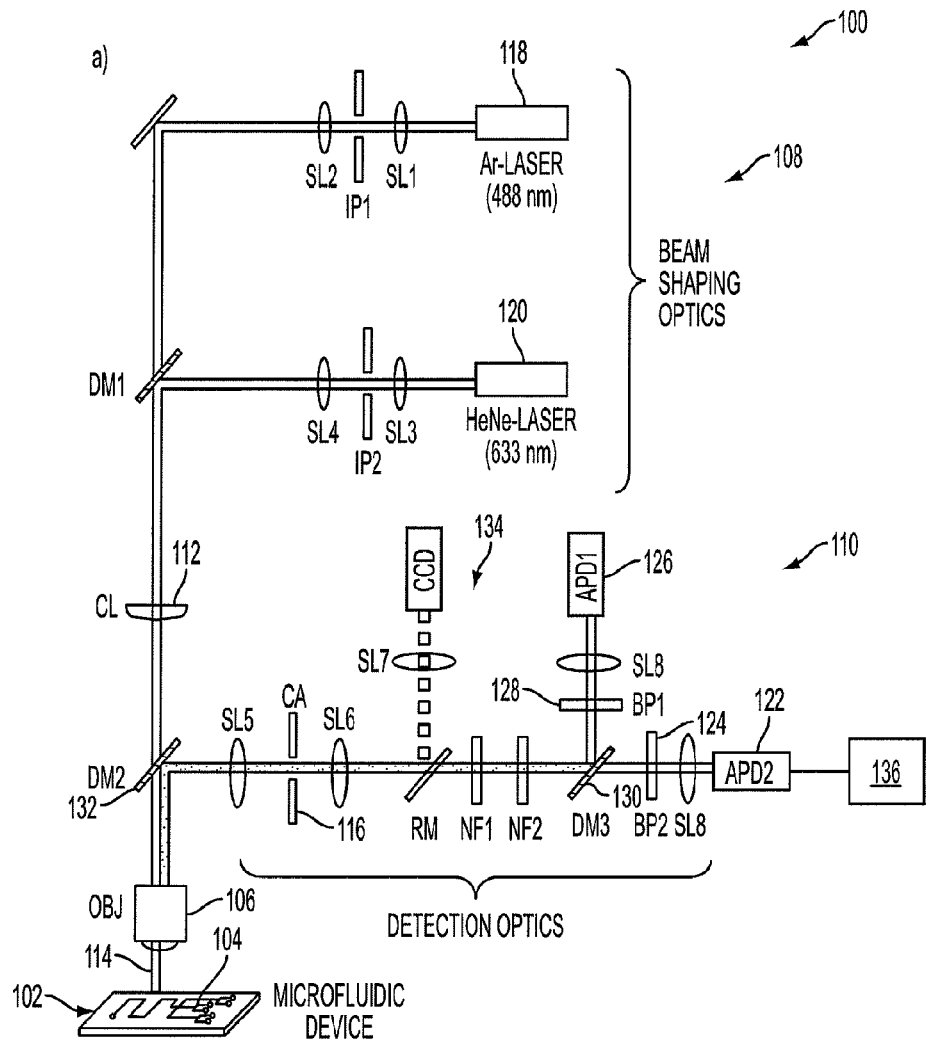
FIGS. 2A-2D illustrated an example of a CICS system that can be used in the system of FIG. 1.

FIG. 2A is a schematic illustration of a cylindrical illumination confocal spectroscopy (CICS) system 100 that can be used for the confocal spectroscopy system 24 according to an embodiment of the current invention (see also U.S. application Ser. No. 12/612,300, the entire contents of which are incorporated herein by reference). The cylindrical illumination confocal spectroscopy system 100 includes a fluidic device 102 having a fluid channel 104 defined therein, an objective lens unit 106 arranged proximate the fluidic device 102, an illumination system 108 in optical communication with the objective lens unit 106 to provide light to illuminate a sample through the objective lens unit 106, and a detection system 110 in optical communication with the objective lens unit 106 to receive at least a portion of light that passes through the objective lens unit 106 from the sample. The illumination system 108 includes a cylindrical lens 112 constructed and arranged to provide a substantially planar illumination beam 114 that subtends across, and is wider than, a lateral dimension of the fluid channel 104. The detection system 110 includes an aperture stop 116 that defines a rectangular aperture having a longitudinal dimension and a transverse dimension. The aperture stop 116 is arranged so that the rectangular aperture is confocal with an illuminated portion of the fluid channel such that the transverse dimension of the rectangular aperture substantially subtends the lateral dimension of the fluid channel without extending substantially beyond the fluid channel. In other words, the longitudinal, or long dimension, of the rectangular aperture is matched to, and aligned with, the illuminated cross section of the fluid channel 104. FIG. 2B shows the illumination light spread out to provide a substantially planar illumination beam 114. By arranging the substantially planar illumination beam 114 so that it extends beyond the edges of the fluid channel 104 the bright central portion can be centered on the fluid channel. The aperture stop 116 can then be used to block light coming from regions outside of the desired illuminated slice of the fluid channel 104.

The fluidic device 102 can be, but is not limited to, a microfluidic device in some embodiments. For example, the fluid channel 104 can have a width and/or depth than is less than a millimeter in some embodiments. The fluidic device can be, but is not limited to, a microfluidic chip in some embodiments. This can be useful for SML-FSHS using very small volumes of sample material, for example. However, other devices and structures that have a fluid channel that can be arranged proximate the objective lens unit 106 are intended to be included within the definition of the fluidic device 102.

The objective lens unit 106 can be a single lens or a compound lens unit, for example. It can include refractive, diffractive and/or gradient refractive index (GRIN) lenses in some embodiments, for example.

The illumination system 108 can include a source of substantially monochromatic light 118 of a wavelength selected to interact in a detectable way with a sample when it flows through the substantially planar illumination beam in the fluid channel 104. For example, the source of substantially monochromatic light 118 can be a laser of a type selected according to the particular application. The wavelength of the laser may be selected to excite particular atoms and/or molecules to cause them to fluoresce. However, the invention is not limited to this particular example. The illumination system 108 is not limited to the single source of substantially monochromatic light 118. It can include two or more sources of light. For example, the illumination system 108 of the embodiment illustrated in FIG. 2A has a second source of substantially monochromatic light 120. This can be a second laser, for example. The second source of substantially monochromatic light 120 can provide illumination light at a second wavelength that is different from the wavelength from the first laser in some embodiments. Additional beam shaping, conditioning, redirecting and/or combining optical components can be included in the illumination system 108 in some embodiments of the current invention. FIG. 2A shows, schematically, an example of some additional optical components that can be included as part of the illumination system 108. However, the general concepts of the current invention are not limited to this example. For example, rather than free space combination of the illumination beam, the two or more beams of illumination light can be coupled into an optical fiber, such as a multimode optical fiber, according to an embodiment of the current invention.

The detection system 110 has a detector 122 adapted to detect light from the sample responsive to the substantially monochromatic light from the illumination system. For example, the detector 122 can include, but is not limited to, an avalanche photodiode. The detection system can also include optical filters, such as a band pass filter 124 that allows a selected band of light to pass through to the detector 122. The pass band of the band pass filter 124 can be centered on a wavelength corresponding to a fluorescent wavelength, for example, for the sample under observation. The detection system 110 is not limited to only one detector. It can include two or more detectors to simultaneously detect two or more different fluorescent wavelengths, for example. For example, detection system 110 has a second detector 126 with a corresponding second band pass filter 128. A dichroic mirror 130 splits off a portion of the light that includes the wavelength range to be detected by detector 126 while allowing light in the wavelength range to be detected by detector 122 to pass through. The detection system 110 can include various optical components to shape, condition, and/or otherwise modify the light returned from the sample. FIG. 2A schematically illustrates some examples. However, the general concepts of the current invention are not limited to the particular example illustrated.

The cylindrical illumination confocal spectroscopy system 100 also has a dichroic mirror 132 that allows at least a portion of illumination light to pass through it while reflecting at least a portion of light to be detected.

The cylindrical illumination confocal spectroscopy system 100 can also include a monitoring system 134 according to some embodiments of the current invention. However, the monitoring system 134 is optional.

In addition, the detection system can also include a signal processing system 136 in communication with the detectors 122 and/or 126 or integrated as part of the detectors. The signal processing system 136 can be the data processing system 22, can be a part of the data processing system 22, or can be additional components depending on the particular application.

Figure 3:
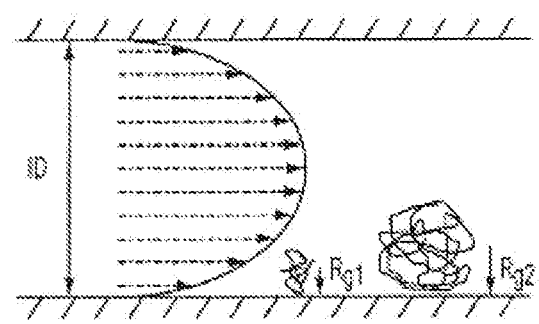
FIG. 3 is a schematic illustration to help explain a possible theoretical mechanism for the hydrodynamic separation.

FIG. 3 is a schematic illustration to help explain a possible hydrodynamic mechanism for the separation of particles according to size. However, the systems and methods of the current invention are not limited to whether or not this theoretical mechanism is correct. It is currently believe that the size separation mechanism is due to a wall exclusion mechanism. In the embodiment of FIG. 1, as particles in the fluid are driven down a buffer-filled fused silica micro-capillary, the larger particles travel faster than the smaller particles. It is believed that this separation occurs due to the wall exclusion mechanism. Pressure-driven flow through the micro-capillary results in Poiseuille flow that is fastest near the channel center and slowest at the walls. This parabolic flow profile is detrimental to separation efficiency in most electrophoretic and chromatographic methods due to Taylor dispersion. However, when the channel size approaches the size of DNA molecules, for example, efficient separation can occur. It has been recently postulated that highest efficiency separation would be obtained when the characteristic channel dimension is ~10× the gyration radius ($R_g$) of the DNA to be separated (Stein D, van der Heyden F H, Koopmans W J, Dekker C. Pressure-Driven Transport of Confined DNA Polymers in Fluidic Channels. Proceedings of the National Academy of Sciences of the United States of America. 2006; 103(43):15853-8). The larger gyration radius of a long DNA molecule limits its ability to sample the low velocity regions near the walls when compared to a short DNA molecule. Thus, long DNA molecules will experience a higher average flow velocity and elute first, in stark contrast to traditional electrophoretic methods where small molecules travel faster. In this regime, we have obtained high efficiency (plate number=$10^5$-$10^6$) and high resolution (37 bp-2.1 kbp) separation of 125 bp-27 kbp DNA ($R_g$=17-550 nm) using a 2 μm ID micro-capillary according to an exemplar embodiment of the current invention. The wide DNA sizing dynamic range seen experimentally indicates that ID:$R_g$ ratio can vary quite significantly while still providing efficient separation (e.g. ID:$R_g$=120:1 to 3.5:1 in previous data).

Although micro-capillaries can be used in the hydrodynamic separation system 12 according to some embodiments of the current invention, poor manufacturing tolerances on commercially available micro-capillaries (e.g. typical IDs of 1±0.5 μm or 2±1 μm from Polymicro Technologies) can be detrimental to reproducibility and size resolution.

Figure 4A:
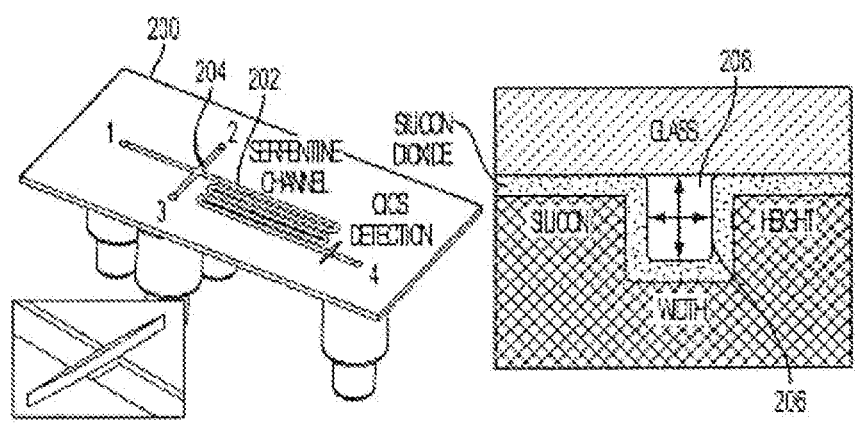
FIG. 4A is a schematic illustration of an embodiment of a microfluidic chip that can be used in the system of FIG. 1 according to some embodiments of the current invention.

FIG. 4A is a schematic illustration of a microfluidic chip 200 according to an embodiment of the current invention. The microfluidic chip 200 defines at least a portion of a fluid channel 202 therein for hydrodynamic separation of particles according to size. In some embodiments of the current invention, the microfluidic chip 200 can be a portion of the hydrodynamic fluid separation system 12 instead of, or in combination with, a micro-capillary.

Theoretically, separation occurs most efficiently when the capillary inner diameter (ID) is nominally 10× larger than the gyration radius of the molecule. In some exemplar embodiments, we have previously obtained 30 bp-2 kbp DNA sizing resolution across the 125 bp-27 kbp range ($R_g$=17 to 550 nm) using a 2 μm ID micro-capillary. This equates to ID:$R_g$ ratios that vary from 120:1 to 3.5:1 across that range. However, manufacturing tolerances on small capillary ID are poor (e.g. 1±0.5 μm or 2±1 μm from Polymicro Technologies), leading to low run-to-run reproducibility. For example, the resolution (R) between the 2 and 2.3 kbp peaks of λ hind iii digest DNA was seen to vary from 1.1 to 3.4 across a 50 m batch of capillary (R=2*($t_1$-$t_2$)/($w_1$+$w_2$), t—elution time and w—peak width). The dimensional variation also had a significant effect on the absolute retention time since fluidic resistance varies with $1/r^4$ where r is the capillary radius. These effects can be significantly reduced through the precision fabrication tolerances achievable in microfluidics. Through micro-fabrication, dimensional tolerances <10% can be routinely obtained. Furthermore, a microfluidic device can permit better control over channel dimensions, geometry, and wall properties. The microfluidic chip 200 can also be integrated with or attached to sample preparation components and/or arrayed detection in some embodiments.

The microfluidic chip 200 has four fluidic ports connected by two micro-channels 202 and 204 arranged in a T-shape. The fluid channel 202 is a serpentine separation channel in the embodiment of FIG. 4A. The fluid channel 202 is located between the T-junction and outlet port 4. The operation of the microfluidic chip 200 is as follows. First, buffer is injected from port 1 to port 4 to prime the long channel. Second, sample is then injected from port 2 to port 3 to prime the short channel. Third, once the device is primed, a picoliter sized plug of DNA sample, for example, is injected from port 2 to port 4. Fourth, following the sample injection, elution buffer is driven from port 1 to port 4 and separation occurs as DNA travels down the serpentine separation channel. Finally, CICS detection is performed after the separation region. Analysis can be performed using TOTO-3 labeled digest DNA or ladder DNA, for example. TE buffer, for example, can be used as the loading, sample, and elution buffers.

Microfluidic devices with separation channels ranging in size from 0.5×0.5 µm to 5×5 µm (w×h) and length from 1 cm to 75 cm, for example, can be fabricated. In one embodiment, the channel surfaces can be thermally grown silicon dioxide 206 and borosilicate glass 208, for example, so that they are chemically similar to a fused silica capillary. The devices can be fabricated by etching 1×1 µm to 5×5 µm (w×h) microfluidic channels into a silicon substrate using $SF_6$ plasma. The wafers can then be thermally oxidized to create a 0.1-1 µm oxide layer. The thickness of the thermal oxide can be used to control the final channel dimensions. After oxidation, fluidic access ports can be drilled into the silicon using an abrasive diamond mandrel. Finally, a borosilicate glass cover can be anodically bonded to the device using annealing temperatures of 250-450° C. and voltages of 500-2500 V. Fluidic connections can be made from the backside using Nanoports (Upchurch).

TABLE 1

Parameters affecting SML-FSHS separation efficiency that can be optimized depending on the application.

| | | | |
|---|---|---|---|
| Device | Channel Height | 0.1-10 µm | The height:$R_g$ ratio determines the DNA size range for which the wall exclusion mechanism is most efficient. |
| | Aspect Ratio | 1:1-25:1 w:h | The aspect ratio affects the symmetry of the flow profile. |
| | Channel Length (cm) | 0.1-500 cm | Channel length determines separation efficiency and time. |
| Operational | Pressure | 1-1000 psi | Pressure affects separation time and molecular conformation. |
| | Temperature | 4-90 °C | Temperature affects diffusion rates and molecular conformation. |
| | Buffer Conditions | pH, strength, composition | Buffer conditions affect molecular distribution, molecular conformation, and wall interactions. |

Device Parameters. Channel geometry is an important factor for some embodiments of the current invention. Key factors can include channel size (width, height, and length), aspect ratio (square, rectangle, and parallel plate), and number of bends. Optimal separation is may occur when ID:$R_g$=10:1, but the invention is not limited to only this particular case. In addition, the wide DNA sizing dynamic range comes from the ability the system to provide highly efficient separation across a wide range of ID: $R_g$ ratios. Smaller channel heights can be more optimal for short DNA while large channel heights can be optimal for long DNA. However, drive pressure increases exponentially with channel height and must be balanced. Furthermore, while microcapillary is radially symmetric, the microchannels will be either square or rectangular. Thus, the aspect ratio (w:h) then becomes critical in determining the flow profile symmetry within the channel. The microchannels also have corner regions with decreased flow that will reduce separation efficiency if the effect is not mitigated. Longer channels can give higher separation efficiency as efficiency increases with $\Delta t$ while axial diffusion increases with $\sqrt{(\Delta t)}$. However, long channels increase analysis time and required drive pressure. Bends can increase the amount of Taylor dispersion. Long separation channels will necessitate a greater number of bends, of which the negative impact must be minimized.

Operational Parameters. In addition to the device parameters, the effect of operational parameters such as drive pressure, temperature, and buffer conditions can also be important for particular applications. Capillary-based free solution separation has been previously shown to display "Van Deemter behavior," typical of chromatography processes. At very low pressures, separation time increases and efficiency decreases due to increased axial diffusion. At very high pressures, separation time decreases while efficiency also decreases, though the mechanisms driving this decrease in efficiency have yet to be elucidated. At high shear rates, it is expected that DNA will be stretched out of the random coil conformation, and an increase in turbulent flow will also result. Temperature can have a significant effect on separation efficiency. Higher temperatures will affect not only axial and radial diffusion, but also the conformation of the DNA molecules and the viscosity of buffer fluid. While the individual effects of temperature can be predicted, the net effect on separation efficiency is complex. In addition, buffer conditions such as pH, ionic strength, and chemical composition can have a large impact on separation efficiency through a multitude of mechanisms. pH and ionic strength will alter the zeta potential of the channel walls and the size of the electron double layer, both of which will affect the distribution of DNA within the channels as well as potential DNA-wall interactions. pH can also affect the net charge of the DNA. At low pH, DNA will be more neutrally charged while at high pH DNA will be more negatively charged. This impacts not only the native conformation of DNA but also its distribution within the microchannel and potential electrostatic interactions with the wall surface. Buffer composition including type of ions ($Na^+$, $K^+$, $Mg^{2+}$, $Cl^{2+}$) as well as buffering species (Phos, TE, TAE, TBE) can also affect the equilibrium DNA conformation.

Some embodiments of the system 10 can further include an alignment system configured to align an illumination beam provided by the cylindrical illumination system 100 with the detection zone 18 of the fluid channel 14. For example, in the case in which a microfluidic chip 200 is included in the hydrodynamic fluid separation system 12, a stage can be included to hold and adjust the position of the microfluidic chip 200. For example, a one-axis, two-axis or three-axis piezo-electric stage can be controlled by a controller to effect movement of the microfluidic chip 200. A sensor system can be included to detect the position of the illumination beam relative to the detection zone 18. For example, a CCD sensor, such as a digital camera sensor can be used according to an embodiment of the current invention. However, the broad concepts of the current invention are not limited to this particular example. In some embodiments, the alignment system can perform the alignment semi-autonomously or completely autonomously such that the system does not require a skilled technician to perform the alignment for each sample.

In an embodiment of the current invention, the alignment system can use image analysis to align the illumination system 24 with the detection zone 18 of the fluid channel 14. In an embodiment, the alignment system can use alignment marks to align the illumination system 24 with the detection zone 18 of the fluid channel 14.

Figure 4B:
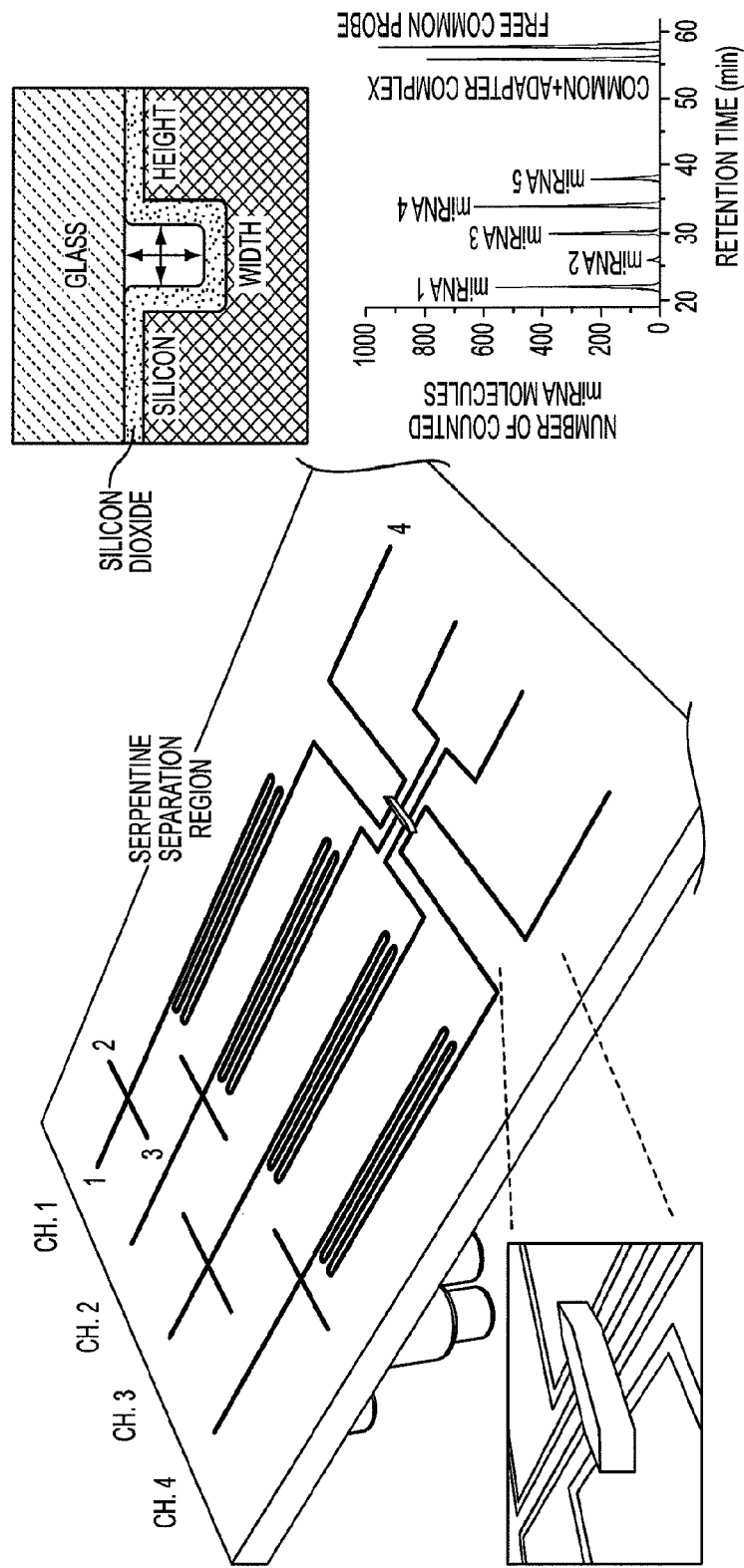
FIG. 4B is a schematic illustration of another embodiment of a microfluidic chip that can be used in the system of FIG. 1 according to some embodiments of the current invention.

FIGS. 1 and 4A illustrate embodiments with a single separation channel. Further embodiments include a plurality of fluid channels which can be illuminated with a single illumination beam so that the separation and detection can be performed in parallel. For example, a plurality of microcapillary tubes can be arranged along side each other across a detection zone. Alternatively, a microfluidic chip can be constructed to have a plurality of fluid channels with detection zones arranged next to each other to be illuminated by a single illumination beam. FIG. 4B is a schematic illustration of an embodiment of a microfluidic chip that has a plurality of separation channels to be operated in parallel, on the same chip.

EXAMPLES

The following provides some examples according to some embodiments of the current invention. The broad concepts of the current invention are limited to the particular examples. In this example, single molecule free solution hydrodynamic separation (SML-FSHS) was performed using the apparatus illustrated in FIG. 1. A small injection chamber was designed to house a 200 µL PCR tube. When pressure was applied to the chamber via the port 38, sample was driven from the tube into the 2 µm ID, 75 cm long, fused silica microcapillary 14. The port 36 was connected to a digital pressure gauge to monitor chamber pressure. Meanwhile, the CICS observation volume was focused into the detection window at the opposite end of the capillary. The laser illumination sheet had a $1/e^2$ diameter of 36 µm, considerably larger than the 2 µm capillary lumen. The confocal aperture, not shown, enabled light collection only from the center 7 µm of the laser line where the illumination was most uniform. In combination, these two elements created a 7×2 µm (w×h) CICS observation volume capable of 100% mass detection efficiency of all molecules within the capillary (Liu, K. J.; Wang, T. H. Biophys J 2008, 95, 2964-75).

To perform a separation, a tube containing TE buffer was first placed into the chamber and used to fill the capillary with loading buffer. The tube was then swapped out for a second tube containing the sample to be analyzed. An ~11 s injection was performed to create a ~5 pL sample plug. Finally, a third tube containing TE elution buffer was placed into the chamber and pressure was applied. In all examples, 100 psi of pressure was used. CICS analysis was performed at the opposite end of the capillary immediately following the final pressure application. Fluorescence data was acquired as a function of time to form a raw avalanche photodiode (APD) fluorescence trace which was analyzed using either bulk fluorescence or single molecule analysis to form a chromatogram. Peak fitting analysis was performed on the final chromatograms to identify the peak parameters.

Figures 5A, 5B, 5C:
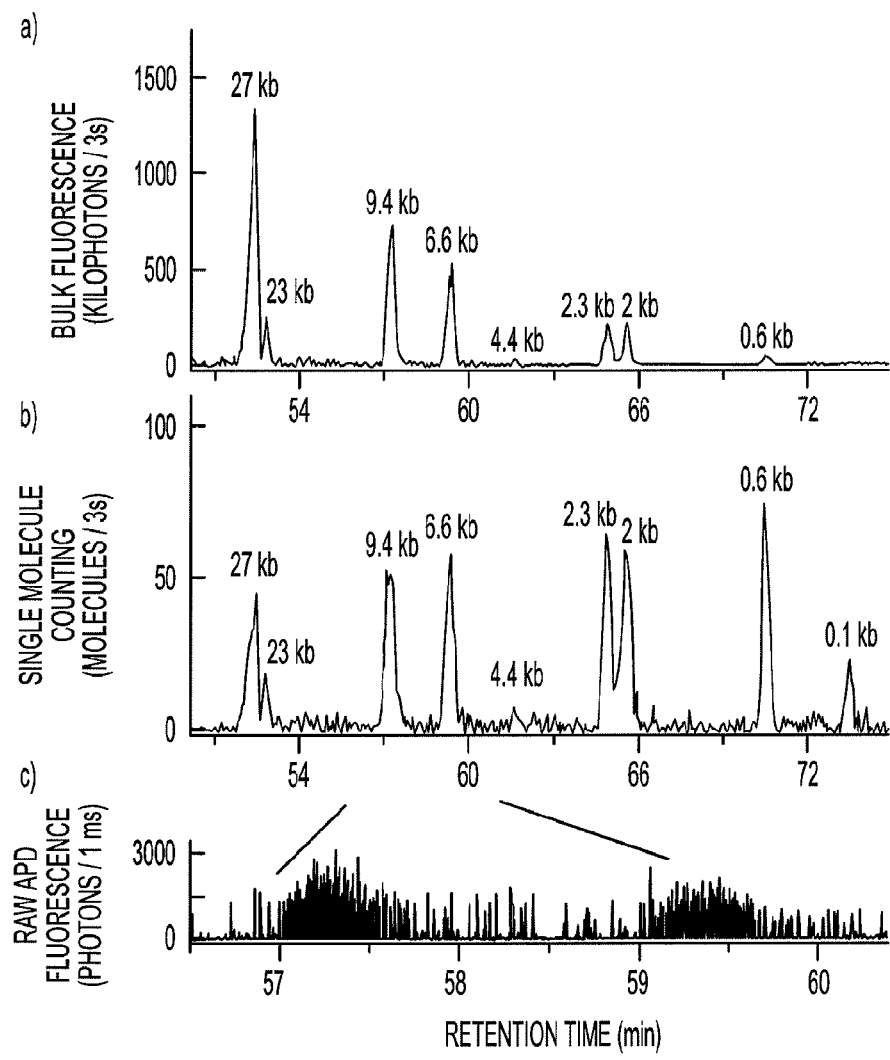
FIGS. 5A-5C show free solution hydrodynamic separation chromatograms of λ Hind iii digest DNA taken using CICS. The raw fluorescence data (FIG. 5C) was analyzed using (FIG. 5A) bulk fluorescence and (FIG. 5B) single molecule counting. Analysis was performed at 5 ng/μL.

FIGS. 5A-5C show chromatograms and raw fluorescence data of TOTO-3 labeled λ Hind iii digest DNA at 5 ng/µL concentration separated using SML-FSHS. Each spike in the raw APD fluorescence data (FIG. 5C) represents a single DNA molecule. A cursory examination of the data shows that within the peak regions there is a high density of single DNA molecules that travel together along the capillary whereas outside the peak regions there is a low number of background molecules. For bulk fluorescence analysis (FIG. 5A), the raw fluorescence data was integrated over 3 s periods to form a chromatogram. For single molecule analysis (FIG. 5B), a thresholding algorithm was used to identify single molecule bursts within the raw fluorescence data. These identified bursts were then summed over 3 s periods to form a chromatogram.

Figure 6:
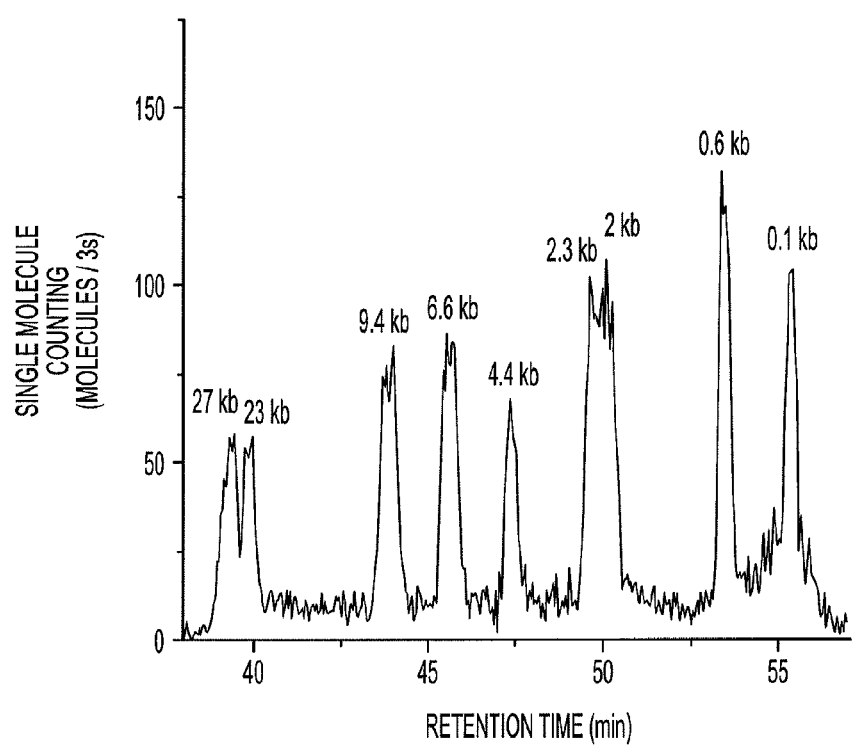
FIG. 6 shows an SML-FSHS chromatogram of λ Hind iii digest DNA according to an embodiment of the current invention. A few differences can be seen compared to FIG. 5B. First, the 0.1 kb peak appears more strongly here. In these data, more complete stripping of the polyimide coating led to lower background (N=32 photons/ms) compared to FIG. 5 (N=84 photons/ms). This results in higher S/N ratio and enhanced detection of the dim 0.1 kb fragments. Second, the 2 kb and 2.3 kb peaks are less well resolved with all peaks eluting at a faster retention times. This is due to the larger capillary ID arising from poor manufacturing tolerances. Finally, the 4.4 kb and 23 kb peaks appear stronger while the 27 kb peak appears weaker. In this run, annealing between the 4.4 kb and 23 kb fragments was reduced by pre-incubation at 65° C. and snap cooling.

Previously reported demonstrations of FSHS were performed at 25 ng/µL, where bulk fluorescence spectroscopy could be used (Wang, X.; Veerappan, V.; Cheng, C.; Jiang, X.; Allen, R. D.; Dasgupta, P. K.; Liu, S. J Am Chem Soc 2010, 132, 40-1). However, at 5 ng/µL, the limitations of bulk FSHS can be seen in FIG. 5A. Because each fragment was present at equal molar ratios, the fluorescent intensity of each peak scaled directly with DNA length. The intensity of the 125 bp peak was hundreds of times lower than that of the 23 kb peak and nearly undetectable by bulk fluorescence. Alternatively, when the same analysis was performed using single molecule FSHS (SML-FSHS), each fragment was detected equally. This can be qualitatively seen in FIG. 5B where all the peaks have comparable size regardless of length. Occasionally, elevated fluorescence background arising from residual polyimide in the detection window can compromise the S/N ratio for the smallest DNA fragments. Though the 125 bp peak appears underrepresented, it is clearly detectable above baseline. The 4 kb fragment is almost entirely absent due to near complete annealing to the 23 kb fragment, creating a new 27 kb fragment. Both bulk and single molecule analysis give nearly identical retention time curves (FIG. 6). Detailed analysis parameters are provided in Table 2.

TABLE 2

Detailed peak fit parameters for the λ Hind iii digest separation given in FIG. 5.

Single Molecule

| DNA Length- L (bp) | Retention Time- t (min) | FWHM- w (s) | Detected Molecules | Plate Number- N | Resolution- R |
|---|---|---|---|---|---|
| 125 | 73.5 | 16.8 | 124 | 382745 | 10.4 |
| 564 | 70.6 | 17.4 | 451 | 329629 | 15.2 |
| 2027 | 65.6 | 22.0 | 435 | 177638 | 1.9 |
| 2322 | 64.9 | 18.8 | 416 | 239551 | 10.2 |
| 4361 | 61.6 | 20.1 | 43 | 187543 | 6.5 |
| 6557 | 59.4 | 21.9 | 413 | 146663 | 5.7 |
| 9416 | 57.3 | 22.7 | 435 | 127199 | 14.6 |
| 23130 | 52.9 | 13.5 | 68 | 307915 | 1.5 |
| 27491 | 52.4 | 27.2 | 361 | 73994 | |

Bulk Fluorescence

| DNA Length- L (bp) | Retention Time- t (min) | FWHM- w (s) | Area | Plate Number- N | Resolution- R |
|---|---|---|---|---|---|
| 125 | 73.7 | 59.9 | 289770 | 30238 | 5.1 |
| 564 | 70.6 | 14.7 | 767005 | 460973 | 19.8 |
| 2027 | 65.6 | 15.5 | 3476380 | 357703 | 2.4 |
| 2322 | 64.9 | 16.7 | 3772320 | 301127 | 13.4 |
| 4361 | 61.6 | 12.7 | 353659 | 469164 | 9.1 |
| 6557 | 59.4 | 17.5 | 8976100 | 230029 | 7.2 |
| 9416 | 57.3 | 17.5 | 13244200 | 213919 | 20.0 |
| 23130 | 52.8 | 8.9 | 2464150 | 701873 | 1.9 |
| 27491 | 52.4 | 20.4 | 25259100 | 131319 | |

The peak parameters obtained by curve-fitting with Origin.
$R = 2*(t_1 - t_2)/(w_1 + w_2)$, $N = 5.55\ t^2/w^2$.

SML-FSHS is unique in that it has a wide dynamic range and is able to separate both long and short DNA within the same run. Conventional methods, such as agarose gel electrophoresis and pulsed field gel electrophoresis, do not possess the same combination of resolution, dynamic range, and sensitivity (Finney, M. Pulsed-Field Gel Electrophoresis; John Wiley & Sons, Inc., 2001; Voytas, D. Agarose Gel Electrophoresis; John Wiley & Sons, Inc., 2001). 23 kb vs. 27 kb fragments can be separated under the same conditions as 2 kb vs. 2.3 kb and 100 bp vs. 200 bp fragments. Given the current configuration (L=75 cm, ID=2 µm, P=100 psi) and results, the minimum sizing resolutions at 125, 2027, and 23130 bp are 37, 147, and 2108 bp, respectively. The separation mechanism is thought to occur through wall exclusion and is non-linear with DNA length (Stein, D.; van der Heyden, F. H.; Koopmans, W. J.; Dekker, C. Proc Natl Acad Sci U S A 2006, 103, 15853-8; Tijssen, R.; Bos, J.; van Kreveld, M. E. Anal Chem 1986, 58, 3036-3044). The finite hydrodynamic radius of each molecule limits its proximity to the wall. When combined with the Poiseuille flow profile, each molecule experiences a different average flow velocity dependent on its size. Higher DNA sizing resolution can be obtained by transitioning to a smaller diameter or longer capillary. 5 nucleotide resolution has been previously demonstrated using a 1 µm ID capillary (Wang, X.; Wang, S.; Veerappan, V.; Byun, C. K.; Nguyen, H.; Gendhar, B.; Allen, R. D.; Liu, S. Anal Chem 2008, 80, 5583-9).

Figure 7:
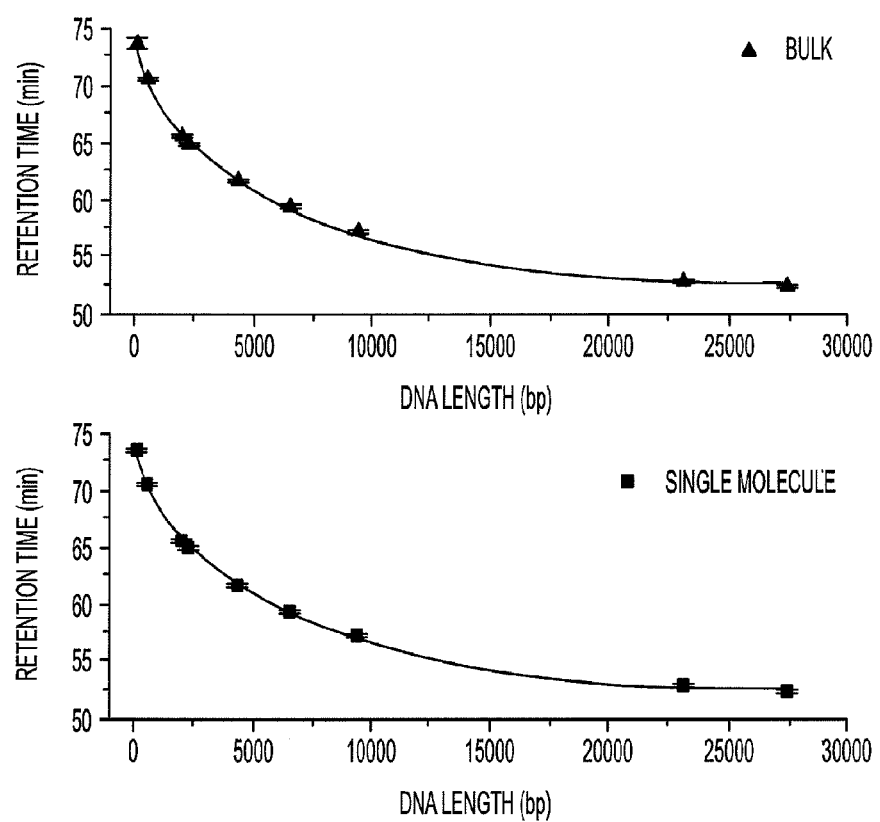
FIG. 7 shows bulk and single molecule retention time curves for the 2 Hind iii digest chromatograms given in FIG. 5. The chromatogram peak parameters were obtained by peak fitting with Origin. Error bars represent peak fit standard deviations. The peak locations were then plotted and fit according to $t=A+B*L^{0.567}+C*L^{1.134}$ where t is the retention time and L is the DNA length in base pairs. The curve-fits show excellent agreement with the model (Tijssen, R.; Bos, J.; van Kreveld, M. E. Anal Chem 1986, 58, 3036-3044; Wang, X.; Veerappan, V.; Cheng, C.; Jiang, X.; Allen, R. D.; Dasgupta, P. K.; Liu, S. J Am Chem Soc 2010, 132, 40-1). Comparable results were obtained from both bulk and single molecule chromatograms as evidenced from the nearly identical fit parameters (Bulk: A=75.18, B=−0.14, C=2.23e-4, $R^2$=0.999. Single Molecule: A=75.42, B=−0.14, C=2.27e-4, $R^2$=0.998). A, the average fluidic transit time, was used for flow velocity calculations.

Significant variations in sizing resolution have been seen from capillary manufacturing tolerances. Resolution between the 2027 and 2322 bp peaks varied from 1.1 to 3.4 across a 50 m batch of capillary. We estimate this was due to a ~0.4 µm variation in capillary ID. This dimensional variation also has a significant effect on absolute retention time which can be reduced through calibration or, perhaps, the precision fabrication tolerances achievable in microfluidics. Additionally, the staining ratio can have adverse effects on the DNA separation efficiency. At higher dye:bp ratios, greater amounts of background DNA were seen between the separated peaks. We suspect this is due to the dimeric TOTO-3 dye stochastically bridging adjacent DNA molecules (Glazer, A. N.; Rye, H. S, Nature 1992, 359, 859-61; Kim, Y.; Morris, M. D. Anal Chem 1994, 66, 1168-74) and creating new, pseudo-randomly sized DNA fragments. This effect can be minimized by optimizing the staining protocol (FIG. 7) or transitioning to a monomeric dye.

Figures 8A, 8B:
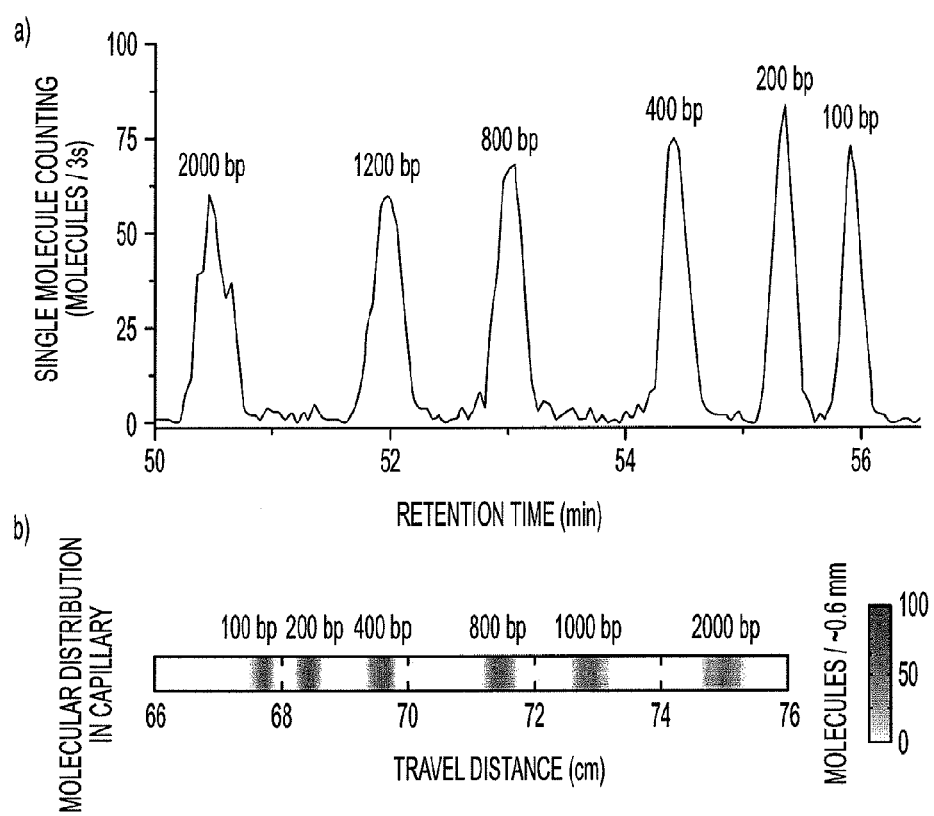
FIGS. 8A-8B show SML-FSHS analysis of a 100 bp DNA ladder using 610 yoctomoles of DNA depicted as (FIG. 8A) a retention time chromatogram and (FIG. 8B) a spatial distribution heat map according to an embodiment of the current invention.
Figures 9A, 9B:
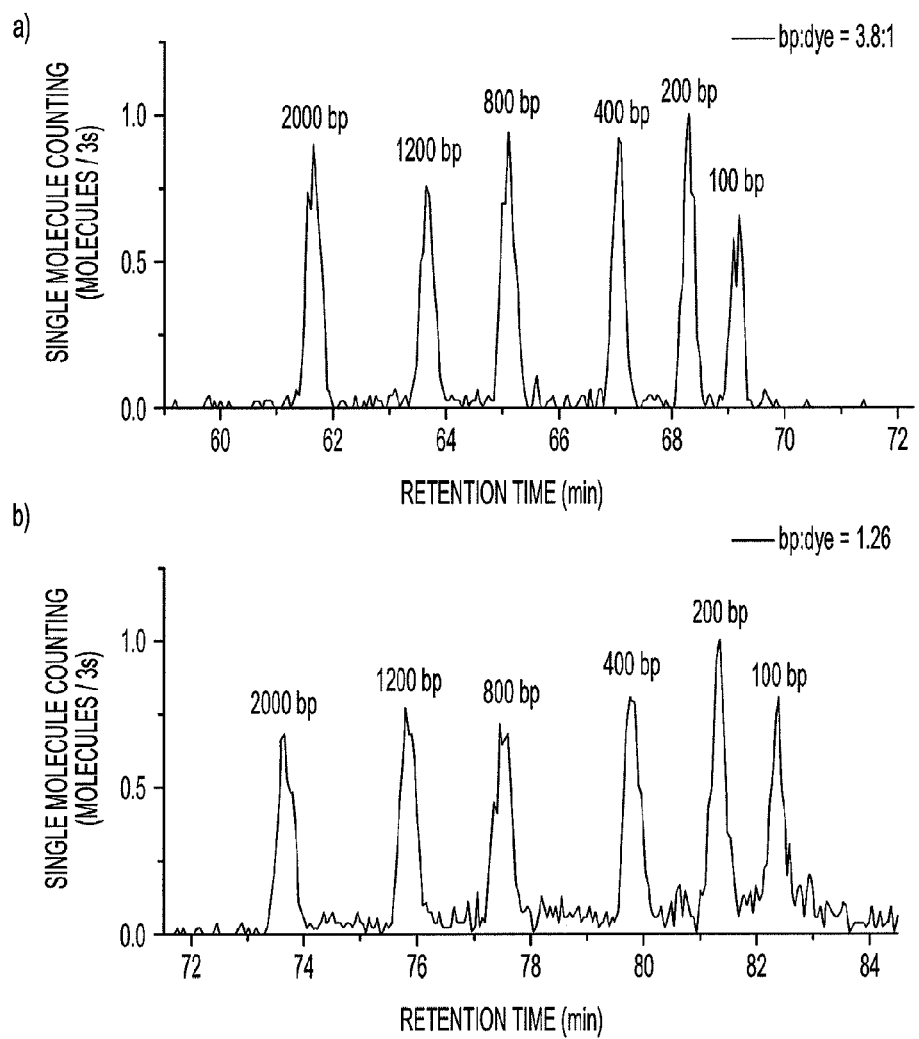
FIGS. 9A-9B show SML-FSHS chromatograms of a 100 bp DNA ladder at (FIG. 9A) 3.8:1 bp:dye staining ratio (0.25 ng/μL DNA and 0.1 μM TOTO-3) vs.

To test the sizing resolution and detection sensitivity, SML-FSHS was performed on a TOTO-3 labeled 100 bp DNA ladder. FIG. 8A shows a single molecule chromatogram taken at 0.25 ng/µL total concentration. Once again each peak appears with equal magnitude. Each of the peaks was fully resolved as the resolution between adjacent peaks varied from 3.0 to 5.9. Calculations of theoretical plate number show that the separation efficiency was also very high. Plate number ranged from 151,000 to 533,000 across the peaks. In other examples, we have attained plate numbers over 1,400,000. The time domain data in FIG. 8A is remapped into a spatial domain heat map in FIG. 8B to illustrate the distribution of molecules as they travel down the capillary. A retention time curve is shown in FIG. 9 along with peak parameters in Table 3.

TABLE 3

Detailed peak fit parameters for the 100 bp ladder separation given in FIG. 8.
Single Molecule

| DNA Length-L (bp) | Retention Time-t (min) | FWHM-w (s) | Detected Molecules | Plate Number-N | Resolution-R |
|---|---|---|---|---|---|
| 100 | 55.9 | 10.8 | 283 | 533140 | 3.0 |
| 200 | 55.3 | 12.0 | 352 | 428036 | 4.3 |
| 400 | 54.4 | 13.9 | 393 | 305741 | 5.9 |
| 800 | 53.0 | 14.8 | 373 | 257251 | 4.0 |
| 1200 | 52.0 | 16.4 | 364 | 201613 | 5.1 |
| 2000 | 50.5 | 18.4 | 357 | 150862 | |

The peak parameters obtained by curve-fitting with Origin.
$R = 2*(t_1 - t_2)/(w_1 + w_2)$, $N = 5.55\ t^2/w^2$.

With a 7.6 pL injection volume, 610 yoctomoles of DNA were analyzed which is 2-3 orders of magnitude lower than standard CE-LIF (Kostal, V.; Katzenmeyer, J.; Arriaga, E. A. Anal Chem 2008, 80, 4533-50; Frost, N. W.; Jing, M.; Bowser, M. T. Anal Chem 2010, 82, 4682-98) and conventional FSHS (Wang, X.; Veerappan, V.; Cheng, C.; Jiang, X.; Allen, R. D.; Dasgupta, P. K.; Liu, S. J Am Chem Soc 2010, 132, 40-1). Quantification was performed by direct single molecule counting without the need for reference samples. Whereas 368±19 DNA molecules were expected, an average of 353±38 molecules was detected in each of the six peaks. If the slightly underrepresented 100 bp peak is excluded, the average increases and the standard deviation decreases to 368±16 molecules, matching the predicted value based on injection volume and Poisson variability. This suggests that, for all but the dimmest molecules, SML-FSHS has 100% mass detection efficiency and high quantification accuracy that is limited predominantly by molecular shot noise (Chen, D.; Dovichi, N. J. Analytical Chemistry 1996, 68, 690-696). This agrees with our previous data that demonstrates 100% mass detection efficiency within a 2 µm deep microchannel (Liu, K. J.; Wang, T. H. Biophys J 2008, 95, 2964-75). The projected limit of detection for the 400 bp peak (S/N=3) approaches 27 yoctomoles (~16 molecules). For small DNA, we have obtained well differentiated chromatograms with as few as 240 yoctomoles (~150 molecules). At lower concentrations, the quantitative accuracy was limited by mass loss within the capillary in addition to molecular shot noise. It is likely that the DNA sizing resolution and detection sensitivity can be further increased through sample stacking methods as in CE.

As a final test, we investigated whether SML-FSHS could be used to enhance a typical single molecule assay. Many solution phase nanosensor assays are designed to be homogeneous because of difficulty in separating unbound probes and fluorophores (Zhang, C. Y.; Yeh, H. C.; Kuroki, M. T.; Wang, T. H. Nat Mater 2005, 4, 826-31). For example, molecular beacon probes are theoretically designed to bind and fluoresce only in the presence of specific DNA target, eliminating the need to remove unbound probes. However, in practice unbound probes stochastically fluctuate between open and closed states even in the absence of target. This difficulty in distinguishing between target-bound beacon and stochastically open beacon increases fluorescence background and reduces assay sensitivity. Many approaches have been taken to reduce background and increase beacon sensitivity (Santangelo, P. J.; Nix, B.; Tsourkas, A.; Bao, G. Nucleic Acids Res 2004, 32, e57; Wang, L.; Yang, C. J.; Medley, C. D.; Benner, S. A.; Tan, W. J Am Chem Soc 2005, 127, 15664-5).

Figure 10:
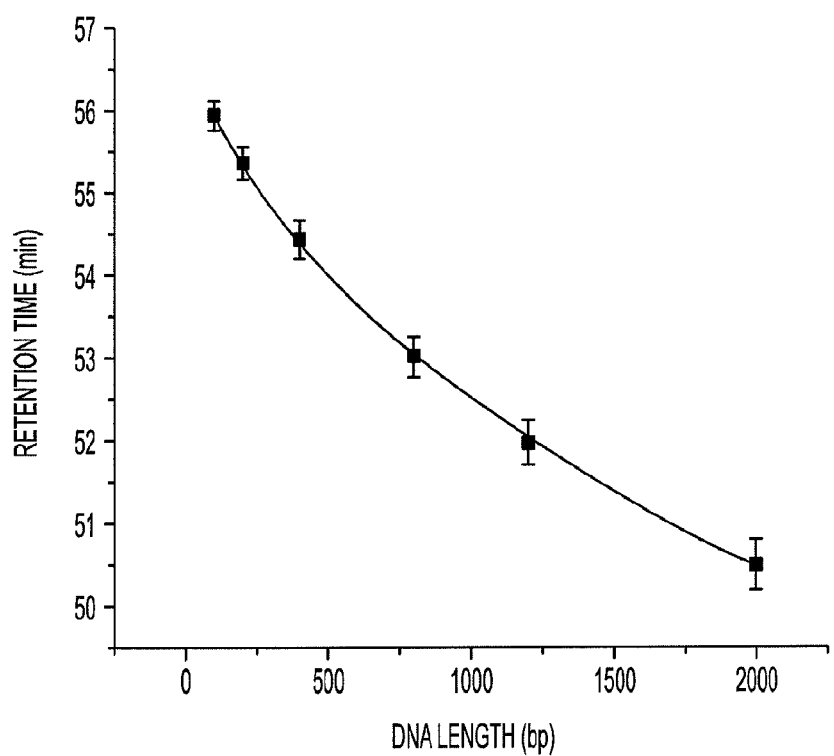
FIG. 10 shows a single molecule retention time curve for the 100 bp ladder chromatograms given in FIGS. 8A-8B. The chromatogram peak parameters were obtained by peak fitting with Origin. Error bars represent peak fit standard deviations. The peak locations were then plotted and fit according to $t=A+B*L^{0.567}+C*L^{1.134}$ where t is the retention time and L is the DNA length in base pairs. The curve-fit (red) shows excellent agreement with the model (Tijssen, R.; Bos, J.; van Kreveld, M. E. Anal Chem 1986, 58, 3036-3044; Wang, X.; Veerappan, V.; Cheng, C.; Jiang, X.; Allen, R. D.; Dasgupta, P. K.; Liu, S. J Am Chem Soc 2010, 132, 40-1). (Single Molecule: A=57.34, B=−0.10, C=1.56e-4, $R^2$=0.999). A, the average fluidic transit time, was used for flow velocity calculations.

A 24 bp molecular beacon was designed to detect a region of the E. coli 16 s rRNA sequence (Xi, C.; Balberg, M.; Boppart, S. A.; Raskin, L. Appl Environ Microbiol 2003, 69, 5673-8). Bulk fluorescence experiments were first performed to verify functionality of the beacon. A serial dilution of the rRNA target was performed from 128 nM down to 0.25 nM and hybridized to 5 nM molecular beacon in TE buffer. A substantial increase in fluorescence was seen when the target concentration was varied from 2 to 128 nM (FIG. 10). Below 2 nM, little change in fluorescence was seen. The high background fluorescence level indicated that even in absence of target, large numbers of beacons remained stochastically open. This was due to the intrinsic theiuiodynamic equilibrium between the conformational states and the lack of $MgCl_2$ in the buffer.

Figure 11:
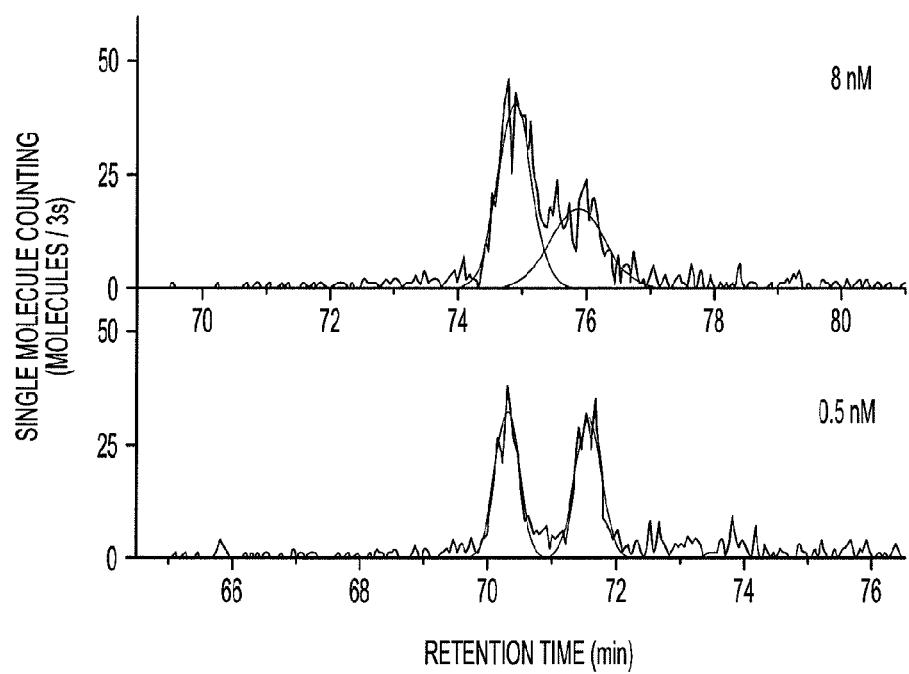
FIG. 11 shows an SML-FSHS analysis of a 16s rRNA target using a molecular beacon according to an embodiment of the current invention. The earlier peak and later peak correspond to target bound beacon and stochastically open beacon, respectively.

For SML-FSHS analysis, the 8 nM target and 0.5 nM target pairs were chosen. FIG. 11 shows the resultant single molecule chromatograms. Peak fits are shown as the smooth lines. The first peak corresponded to the larger target bound molecular beacon complex while the second peak corresponded to the smaller beacon only complex. Any signal present in the second peak could only arise from beacons that were stochastically open. Closed beacons and unbound target could not be seen. A slight shift in retention time is seen due to capillary ID variation.

From the data, it is evident why the sensitivity of the molecular beacon decreases so rapidly below 1 nM. As the target concentration decreased, the number of target bound beacons decreased ($1^{St}$ peak) while the number of stochastically open beacons remained constant ($2^{nd}$ peak). At 0.5 nM target concentration, the number of target bound beacons and stochastically open beacons was nearly equal at 303 and 314 molecules, respectively. In the absence of separation, these bursts are indistinguishable from one another and the fluorescent background swamps out the target induced signal. However, with SML-FSHS the true signal can be resolved from background based on size of the bound complex. Thus, this method can be used to optimize nanosensor design at low target concentrations and potentially be extended to heterogeneous single molecule assays to separate unbound background probes.

In conclusion, we have demonstrated SML-FSHS, a method that cohesively integrates a simple and high resolution size based separation with high sensitivity single molecule analysis. Because of the seamless integration between the low mass loss separation method and high mass detection efficiency CICS, analysis could be performed using only yoctomoles of DNA and picoliters of sample. With further development, this method could be applied to a bevy of applications where CE and HPLC are currently utilized but with greatly reduced cost due the simple apparatus and materials that are required. The wide dynamic range could enable new applications where slower and less sensitive methods such as pulsed field gel electrophoresis are used. Each run consumes only minute amounts of standard buffers and sample. Capillaries are inexpensive and require no special preparation. Separation requires only a small chamber and simple pressure control. The CICS detection system is no more complex than a standard LIF system. Furthermore, SML-FSHS can also be used in single molecule assays to improve sensitivity and specificity by reducing background and increase assay content through multiplex analysis. New single molecule assays can be designed that are heterogeneous in format since separation and detection are cohesively coupled. Finally, due to the simple separation apparatus and design, throughput can be easily enhanced by utilizing capillary arrays or microfluidic formats.

Some features of some embodiments of the current invention can be summarized, as follows:

High DNA sizing resolution—SML-FSHS has high DNA sizing resolution that is comparable to capillary electrophoresis. Resolution down to 30 bp for dsDNA and 5 nt for short oligonucleotides has been achieved. Further increases in sizing resolution can likely be obtained through optimization.

Wide sizing dynamic range—SML-FSHS can be used to size small DNA (100 bp vs. 200 bp), medium DNA (2 kbp vs. 2.3 kbp), and large DNA (23 kbp vs. 27 kbp) simultaneously within the same run. No other DNA sizing and separation method has comparable dynamic range while maintaining high DNA sizing resolution.

High detection sensitivity—Because single molecule analysis is performed rather than bulk fluorescence, SML-FSHS can be performed with as little as $10^{-22}$ moles of DNA (100 molecules). This rivals or surpasses the limit of detection achieved with state of the art capillary electrophoresis.

High quantitative accuracy—Because the CICS laser detection volume envelops the entire lumen of the separation capillary, all molecules are detected with 100% mass detection efficiency. This is in contrast to standard laser induced fluorescence where the detection laser spot is considerably smaller than the separation capillary, compromising detection efficiency and sensitivity. CICS based detection ensures that all molecules are counted, and no molecules are missed. Because all molecules are individually counted on a single molecule basis, no calibration or reference curves are necessary. Furthermore, CICS reduces detection artifacts due to capillary drift which can be significant when the laser detection volume is smaller than the separation capillary. Finally, the uniformity of the CICS detection volume reduces signal variability, further increasing quantitative accuracy.

Low sample consumption—SML-FSHS effectively realizes the promise of zero sample consumption. Each analysis consumes only 5 pL of sample. This is approximately 100× less than typical capillary electrophoresis.

No sieving media or capillary wall coatings—Unlike capillary electrophoresis, gel electrophoresis, or HPLC, no sieving media, polymer gels, or capillary coatings are necessary. Because separation is based on size alone, rather than dielectric properties, all that is necessary is a bare, fused silica capillary and a simple buffer such as TE. This greatly reduces expense and complexity.

No high voltage power supply—High voltage power supplies and complex injection schemes are also unnecessary. All that the SML-FSHS system requires to drive the sample and separation is a simple pressure source such as bottled nitrogen or compressed air.

Low cost—The SML-FSHS system requires only an inexpensive bare silica capillary, a small sample injection chamber and a simple pressure source to perform separation. This is in contrast to capillary electrophoresis systems which require high voltage power supplies, derivatized separation capillaries, and polymer sieving matrices for separation.

The examples of an SML-FSHS system according to embodiments of the current invention was used to size and separate DNA using a micron sized capillary. Other embodiments incorporate a microfluidic device for separation rather than a capillary. This can increase the sample processing and analysis capabilities of the platform since other microfluidic elements can be tied in either directly upstream or downstream of the separation system. For example, the FSHS element can be combined with a microfluidic droplet platform for sample processing or PCR analysis. Furthermore, platform throughput can be enhanced because multiple separation channels can be incorporated on the same device to form an array.

Although in examples according to some embodiments of the current invention performed DNA analysis, separation of other biomolecules, such as proteins, peptides, RNA, lipids, vesicles, and organelles, can also be performed. With suitable capillary or microfluidic components, it is anticipated that separation of sugars, polymers, pharmaceutical compounds, and metabolites can also be performed. The scope of some embodiments of the current invention can extend beyond molecular biology and into analytical chemistry, for example.

In another embodiment, capillaries or microfluidic channels may be surface functionalized with moieties that interact with the separated molecules to enhance the distinction between molecules beyond size alone. For example, it is possible that chiral molecules or enantiomers may be separated if the inner surface of the capillary is coated with a compound that reacts differentially with the R- and L isomers.

SML-FSHS systems according to some embodiments of the current invention can have a large number of commercial uses. For example, one use is the sizing and separation of DNA as previously described. Thus, any application that requires high sensitivity and high resolution DNA sizing analysis could use this platform rather than capillary electrophoresis or gel electrophoresis. This could be in research applications such as cancer, genomics, proteomics, cell and molecular, and chemistry or diagnostic applications such as biomarker detection, mutation analysis, and genotyping. Furthermore, it could also be used in non-research applications such as forensic analysis.

The system according to some embodiments of the current invention can be used to separate any molecules based on size. Thus, SML-FSHS could be applied in areas such as pharmaceutical research to separate active isomers, analytical chemistry to separate chemical compounds, and biodefense to identify dangerous pathogens and biothreats, for example.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of separating, detecting and determining a size of each of a plurality of particles in a fluid, comprising:
   compelling said fluid to flow through a fluid channel such that larger particles of said plurality of particles travel through said fluid channel faster than smaller particles of said plurality of particles;
   illuminating a detection zone of said fluid channel substantially uniformly across an entire cross section of said fluid channel such that each of said plurality of particles passes through illumination light upon passing through said detection zone;
   detecting each of said plurality of particles based on corresponding responses to said illuminating to determine a time that each of said plurality of particles passes through said detection zone; and
   determining a size of each of said plurality of particles based on said time that each of said plurality of particles passes through said detection zone,
   wherein said detection comprises quantification of said plurality of particles, and
   wherein said quantification is quantification by analyzing aggregate signals to correlate said aggregate signals with a quantity of particles in said plurality of particles.

2. The method of claim 1, wherein said plurality of particles is a plurality of molecules.

3. The method of claim 1, wherein said plurality of particles comprises at least one of polymer, pharmaceutical, fluorophore, DNA, RNA, lipid, emulsion, carbohydrate, metabolite, antibody, or protein molecules, vesicle or cells.

4. The method of claim 1, wherein said plurality of particles is between 1 to $10^6$ molecules in 1 pL to 1 µL of a sample.

5. The method of claim 1, wherein said fluid channel is defined by a capillary.

6. The method of claim 1, wherein said fluid channel is defined by a microfluidic chip.

7. The method of claim 6, wherein said fluid channel defines a plurality of fluid channels.

8. The method of claim 1, wherein said compelling is applying a pressure to said fluid.

9. The method of claim 1, wherein said illuminating is illuminating with a cylindrical illumination system.

10. The method of claim 1, further comprising collecting said plurality of particles after being separated in fractions based on time or size.

11. A system for separating, detecting and determining a size of each of a plurality of particles in a fluid, comprising:
    a hydrodynamic fluid separation system comprising a fluid channel;
    an illumination system arranged to illuminate a detection zone of said fluid channel substantially uniformly across an entire cross section of said fluid channel such that each of said plurality of particles passes through illumination light upon passing through said detection zone;
    a detection system arranged to detect each of said plurality of particles based on corresponding responses to said illumination light to determine a time that each of said plurality of particles passes through said detection zone; and
    a data processing system adapted to communicate with said detection system and configured to determine a size of each of said plurality of particles based on said time that each of said plurality of particles passes through said detection zone,
    wherein said detection system also is configured to quantify a number of particles in said plurality of particles, and
    wherein said quantification is quantification by analyzing aggregate signals to correlate said aggregate signals with a quantity of particles in said plurality of particles.

12. A system for separating, detecting and determining a size of each of a plurality of particles in a fluid according to claim 11, further comprising a pressure application and control system operatively connected to said hydrodynamic fluid separation system.

13. A system for separating, detecting and determining a size of each of a plurality of particles in a fluid according to claim 11, wherein said illumination system is a cylindrical illumination system.

14. A system for separating, detecting and determining a size of each of a plurality of particles in a fluid according to claim 13, further comprising an alignment system configured to align an illumination beam provided by said cylindrical illumination system with said detection zone of said fluid channel.

15. A system for separating, detecting and determining a size of each of a plurality of particles in a fluid according to claim 11, wherein said hydrodynamic fluid separation system comprises a micro-capillary that defines at least a portion of said fluid channel therein.

16. A system for separating, detecting and determining a size of each of a plurality of particles in a fluid according to claim 11, wherein said hydrodynamic fluid separation system comprises a microfluidic chip that defines at least a portion of said fluid channel therein.

17. A system for separating, detecting and determining a size of each of a plurality of particles in a fluid according to claim 11, wherein said hydrodynamic fluid separation system comprises a plurality of fluid channels.

18. A system for separating, detecting and determining a size of each of a plurality of particles in a fluid according to claim 17, wherein said detection system is configured to detect said plurality of fluid channels in parallel simultaneously.

19. A system for separating, detecting and determining a size of each of a plurality of particles in a fluid, comprising:
- a hydrodynamic fluid separation system comprising a fluid channel;
- an illumination system arranged to illuminate a detection zone of said fluid channel substantially uniformly across an entire cross section of said fluid channel such that each of said plurality of particles passes through illumination light upon passing through said detection zone;
- a detection system arranged to detect each of said plurality of particles based on corresponding responses to said illumination light to determine a time that each of said plurality of particles passes through said detection zone; and
- a data processing system adapted to communicate with said detection system and configured to determine a size of each of said plurality of particles based on said time that each of said plurality of particles passes through said detection zone, wherein said hydrodynamic fluid separation system comprises a plurality of fluid channels, each having a respective detection zone arranged to be illuminated substantially uniformly across an entire cross-sectional region of each said respective detection zone by said illumination system, wherein said detection system is configured to detect each of a plurality of particles that pass through each of said respective detection zone based on corresponding responses to said illumination system to determine a time that each of said plurality of particles passes through each said respective detection zone, wherein said data processing system is further configured to determine a size of each of said plurality of particles based on said time that each of said plurality of particles passes through each said respective detection zone to process a plurality of fluid samples in parallel, and wherein said detection system is configured to detect said plurality of fluid channels serially by scanning across said channels.

* * * * *